(12) United States Patent
Biondo et al.

(10) Patent No.: US 10,729,328 B2
(45) Date of Patent: Aug. 4, 2020

(54) OPTICAL BASED IMPAIRMENT DETECTION SYSTEMS AND METHODS

(71) Applicant: GM Global Technology Operations LLC, Detroit, MI (US)

(72) Inventors: William A. Biondo, Beverly Hills, MI (US); David T. Proefke, Troy, MI (US); Thomas M. Forest, Macomb, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 428 days.

(21) Appl. No.: 15/603,809

(22) Filed: May 24, 2017

(65) Prior Publication Data

US 2018/0338685 A1  Nov. 29, 2018

(51) Int. Cl.
*A61B 5/00* (2006.01)
*A61B 5/18* (2006.01)
*A61B 5/1455* (2006.01)

(52) U.S. Cl.
CPC .............. *A61B 5/0075* (2013.01); *A61B 5/18* (2013.01); *A61B 5/4845* (2013.01); *A61B 5/1455* (2013.01)

(58) Field of Classification Search
CPC ....... A61B 5/0075; A61B 5/18; A61B 5/4845; G01N 21/47
See application file for complete search history.

(56) References Cited

U.S. PATENT DOCUMENTS

| 2003/0076508 | A1* | 4/2003 | Cornsweet | A61B 3/152 356/517 |
| 2007/0123759 | A1* | 5/2007 | Grata | A61B 5/1112 600/310 |
| 2014/0180041 | A1* | 6/2014 | Li | A61B 5/14558 600/319 |

* cited by examiner

*Primary Examiner* — Eric F Winakur
*Assistant Examiner* — Abid A Mustansir

(57) ABSTRACT

An impairment detection system is provided and includes an emitter, first and second beam selectors, a reference reflector, a sensor and a control module. The emitter is configured to emitter a first light signal. The first beam selector is configured to forward the first light signal to a touch probe. The reference reflector is configured to reflect the first light signal received from the first beam selector to generate a second reflected signal. The second beam selector is configured to receive (i) a first reflected signal from the touch probe based on reflection of the first light signal on an area of a person, and (ii) the second reflected signal. The sensor is configured to receive from the second beam selector the first reflected signal and the second reflected signal. The control module is configured to determine an impairment level of the person based on an output of the sensor.

19 Claims, 12 Drawing Sheets

US 10,729,328 B2

OPTICAL BASED IMPAIRMENT DETECTION SYSTEMS AND METHODS

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to impairment detection systems.

An impairment detection system for determining, for example, an alcohol level of an individual may include a light source, a touch probe, a beam splitter, two multi-spectral sensors (a reference sensor and a finger sensor) and a controller. During operation, a person being tested touches the touch probe. The light source emits a light signal having frequencies to excite alcohol molecules in a bloodstream of the person being tested. The light signal is directed to the touch probe and the reference sensor via the first beam splitter and corresponding fiber optic cables. The touch probe emits the first light signal as a laser beam, which is directed at a finger of the person. The laser beam excites alcohol molecules in the finger of the person and is reflected back as a reflected light signal to the touch probe. The reflected light is directed via a fiber optic cable to the finger sensor. The controller determines an alcohol level of the person based on outputs of the reference sensor and the finger sensor.

SUMMARY

An impairment detection system is provided and includes an emitter, a first beam selector, a reference reflector, a second beam selector, a sensor and a control module. The emitter is configured to emitter a first light signal. The first beam selector is configured to forward the first light signal to a touch probe. The reference reflector is configured to reflect the first light signal received from the first beam selector to generate a second reflected signal. The second beam selector is configured to receive (i) a first reflected signal from the touch probe based on reflection of the first light signal on an area of a person, and (ii) the second reflected signal. The sensor is configured to receive from the second beam selector the first reflected signal and the second reflected signal. The control module is configured to determine an impairment level of the person based on an output of the sensor.

In other features, an impairment detection system is provided and includes an emitter, a first beam selector, a second beam selector, a sensor and a control module. The emitter is configured to emitter a first light signal. The first beam selector is configured to forward the first light signal to a touch probe. The second beam selector is configured to receive the first light signal and a reflected light signal from the touch probe based on reflection of the first light signal on an area of a person. The sensor is configured to receive from the second beam selector the first light signal and the reflected light signal. The control module is configured to determine an impairment level of the person based on an output of the sensor.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

An impairment detection system can include multiple multi-spectral sensors and other components. The multi-spectral sensors tend to be large and expensive. Sensitivities of the multi-spectral sensors tend to drift over time and outputs of the sensors tend to drift based on temperature. Also, differences between the outputs of two multi-spectral sensors tend to drift over time. A first one of the multi-spectral sensors (or reference sensor) is used as a reference to normalize an output of a second multi-spectral sensor (or finger sensor).

Impairment detection systems are set forth herein that include fewer sensors and components than traditional impairment detection systems. Disclosed embodiments include use of only a single multi-spectral sensor and thus include fewer multi-spectral sensors than traditional impairment detection systems. The disclosed impairment detection systems may be used to determine a chemical level (e.g., an alcohol level or level of some other chemical) of a person. The impairment detection systems may also be used to determine a level of a chemical compound or drug (e.g., tetrahydrocannabinol, cocaine, etc.). As an example, the impairment detection systems may be used to scan employees of a company as the employees are checking into work and indicate whether the employees are authorized to work or should be sent home based on respective impairment levels of the employees. As another example, the impairment detection system may be used to scan people prior to and/or upon entering a vehicle (an automobile, an airplane, a train, a boat, etc.) and prevent a person from entering and/or operating a vehicle if an impairment level of the person is greater than a predetermined threshold.

Figure 1:
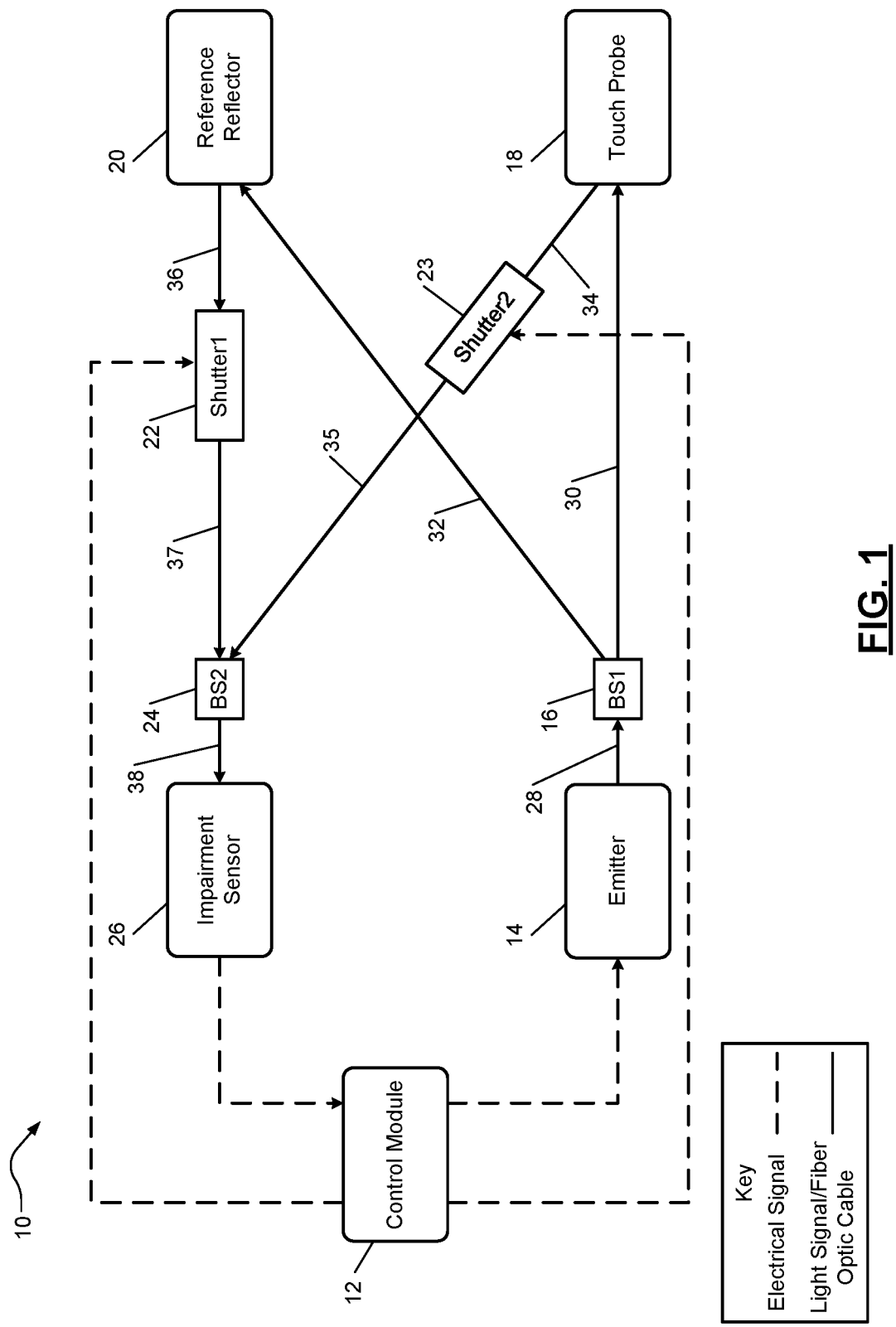
FIG. 1 is a functional block diagram of an example of a first impairment detection system including a reference reflector and multiple shutters in accordance with an embodiment of the present disclosure.

FIG. 1 shows a first impairment detection system 10 that includes a control module 12, an emitter 14, a first beam selector 16, a touch probe 18, a reference reflector 20, a first shutter 22, a second shutter 23, a second beam selector 24 and an impairment sensor 26 (e.g., a finger sensor or other suitable impairment sensor). The emitter 14 is a light beam or laser source that emits light at preselected frequencies and having preselected wavelengths to excite molecules in a bloodstream of a person. The preselected frequencies and other parameters, such as amplitudes, duty cycles, power level at each frequency, etc. may be determined for one or more chemicals and/or drugs. For example, if an alcohol level is being detected, the emitter 14 emits light having wavelengths of 1400-2600 nanometers (nm). In one embodiment, the emitter 14 emits infrared light in the range of 430 tera-hertz (THz) to 300 giga-hertz (GHz)). In one embodiment, light having wavelengths between 300-2600 nm is emitted. Light signals having frequencies outside the infrared spectrum may be emitted. One or more signals, each of which include one or more frequencies, may be emitted during a same period of time or the control module 12 may control the emitter to sequence through a predetermined pattern of frequencies and/or other parameters. The emitter 14 may include one or more light sources, one or more lasers, one or more mirrors, etc.

The touch probe 18 may emit and receive reflected light from excited molecules in an area on a person. Each of the beam selectors 16, 24 includes a beam splitter, a digital micromirror device (DMD), or other beam selecting components. As a first example, each of the beam selectors 16, 24 may be a beam splitter. As another example, the first beam selector 16 may be a DMD, which may be actuated by the control module 12. The control module 12 may control an angular position of a mirror of the DMD. The second beam selector 24 may also be controlled by the control module 12, such as when the second beam selector 24 includes a DMD. In one embodiment, the beam selector 24 operates as a combiner. The beam selectors 16, 24 may include mirrors (e.g., half silver mirrors). The beam selectors 16, 24 may operate as beam steering devices and (i) direct ends of fiber optic cables 30, 32 to an end of fiber optic cable 28 or vice versa, and/or (ii) direct ends of fiber optic cables 35, 37 to an end of fiber optic cable 38 or vice versa. In another embodiment, the beam selectors 16, 24 include galvanometer based beam positioners or other beam selectors and/or beam steering devices.

The shutters 22, 23 have ON and OFF states, permit passage of light when in the ON state, and prevent passage of light when in the OFF state. Although the shutters 22, 23 are shown between (i) the second beam selector 24 and (ii) the touch probe 18 and the reference reflector 20, the shutters 22, 23 may be located between (a) the first beam selector 16 and (b) the touch probe 18 and the reference reflector 20. The reference reflector 20 may include a mirror, a plate having a reflective painted surface, and/or other reflective components. The reference reflector 20 and the fiber optic cables 32, 36, 37 provide a reference channel on which a reflected (or reference) light signal is provided to indicate parameters of the first light signal. This allows the control module 12 to account for drift over time and/or drift due to changes in temperature.

The control module 12 signals the emitter 14, which is a light beam (or laser) source to emit a light signal. The light signal is transmitted via a first fiber optic cable 28 to the first beam selector 16. The light signal is split and provided to both the touch probe 18 via a second fiber optic cable 30 and to the reference reflector via a third fiber optic cable 32. The touch probe 18 emits the light signal and receives reflected light, which is transmitted via fiber optic cables 34, 35 through the second shutter 23 to the second beam selector 24. The light signal provided to the reference reflector 20 is reflected by the reference reflector 20 through the shutter 22 to the second beam selector 24 via fiber optic cables 36, 37. The reference reflector 20 reflects the light from the fiber optic cable 32 to the fiber optic cable 36. The light signals received at the second beam selector 24 are provided to the impairment sensor 26 via fiber optic cable 38. The fiber optic cables 28, 30, 34, 35, 36, 37, 38 and other fiber optic cables disclosed herein optically couple corresponding devices, such as emitters, beam selectors, touch probes, shutters, attenuators, reference reflectors, and impairment sensors. The impairment sensor 26 is a multi-spectral sensor that operates as both a reference sensor to detect an output of a reference channel associated with the reference reflector 20 and as a measurement sensor to detect an output of a user channel associated with the touch probe 18.

The control module 12 controls operation of the shutters, such that the second beam selector 24 receives either a light signal from the first shutter 22 or from the second shutter 23, but not from both shutters 22, 23 during a same period of time. The shutters 22, 23 allow for rapid selection of the outputs of the reference and user channels. This allows for quick periodic detections of the outputs of the reference and user channels. The control module 12 receives outputs of the impairment sensor and, based on the outputs, determines an impairment level of the person being scanned.

Figure 2:
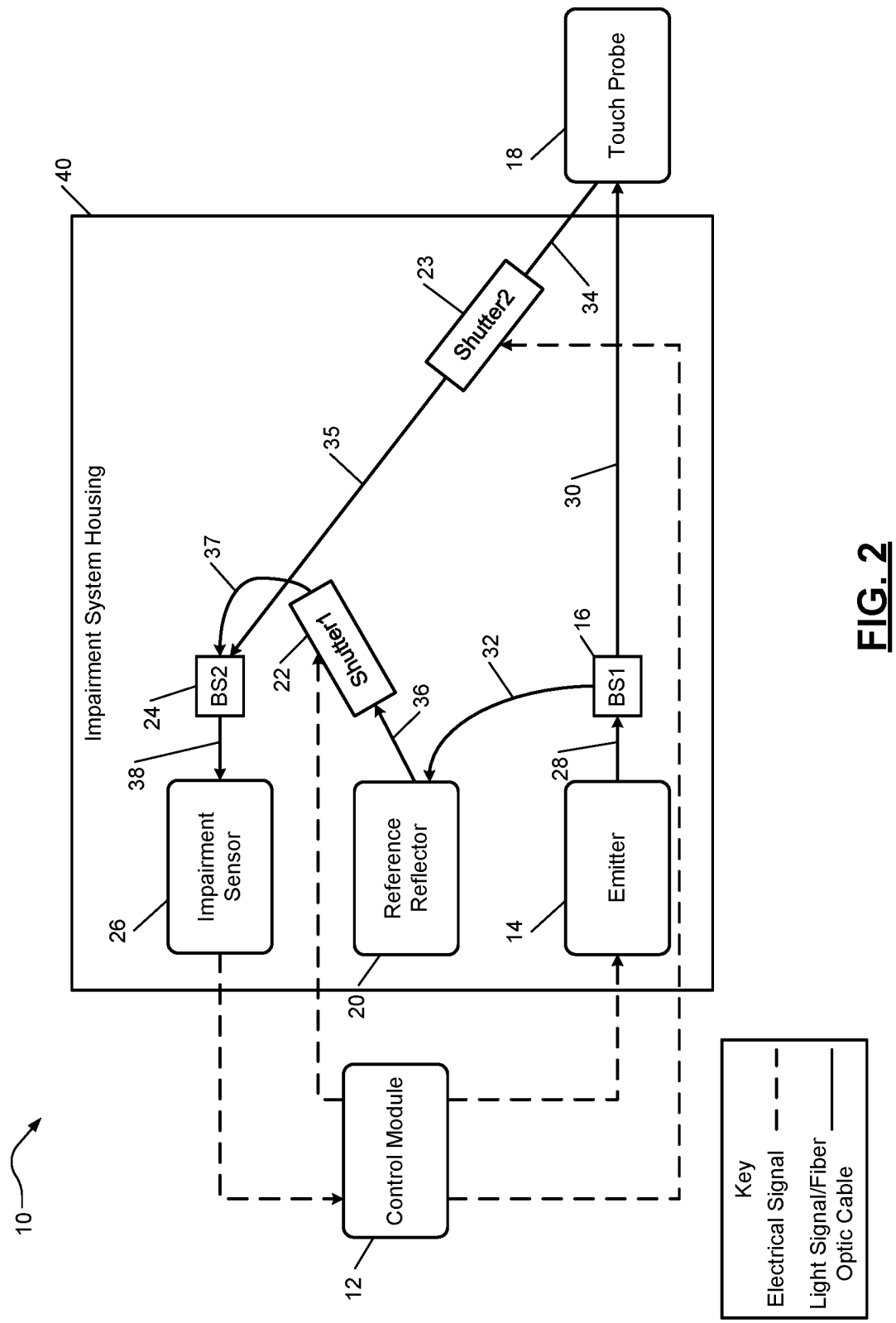
FIG. 2 is a functional block diagram of the first impairment detection system of FIG. 1 illustrating an example packaging embodiment of the present disclosure.

FIG. 2 shows the first impairment detection system 10 where at least a portion of the first impairment detection system 10 is packaged according to an embodiment of the present disclosure. The first impairment detection system 10 includes the control module 12, the emitter 14, the first beam selector 16, the touch probe 18, the reference reflector 20, the first shutter 22, the second shutter 23, the second beam selector 24, the impairment sensor 26 and the fiber optic cables 28, 30, 32, 34, 35, 36, 37, 38.

The emitter 14, beam selectors 16 24, reference reflector 20, shutters 22, 23, and impairment sensor 26 may be included in an impairment system housing 40. Since the impairment detection system 10 includes a single sensor (i.e. the impairment sensor 26), the envelope and volume of the impairment system housing 40 is minimized. In one embodiment, the control module 12 and/or the touch probe 18 are also included in the impairment system housing 40.

Figure 3:
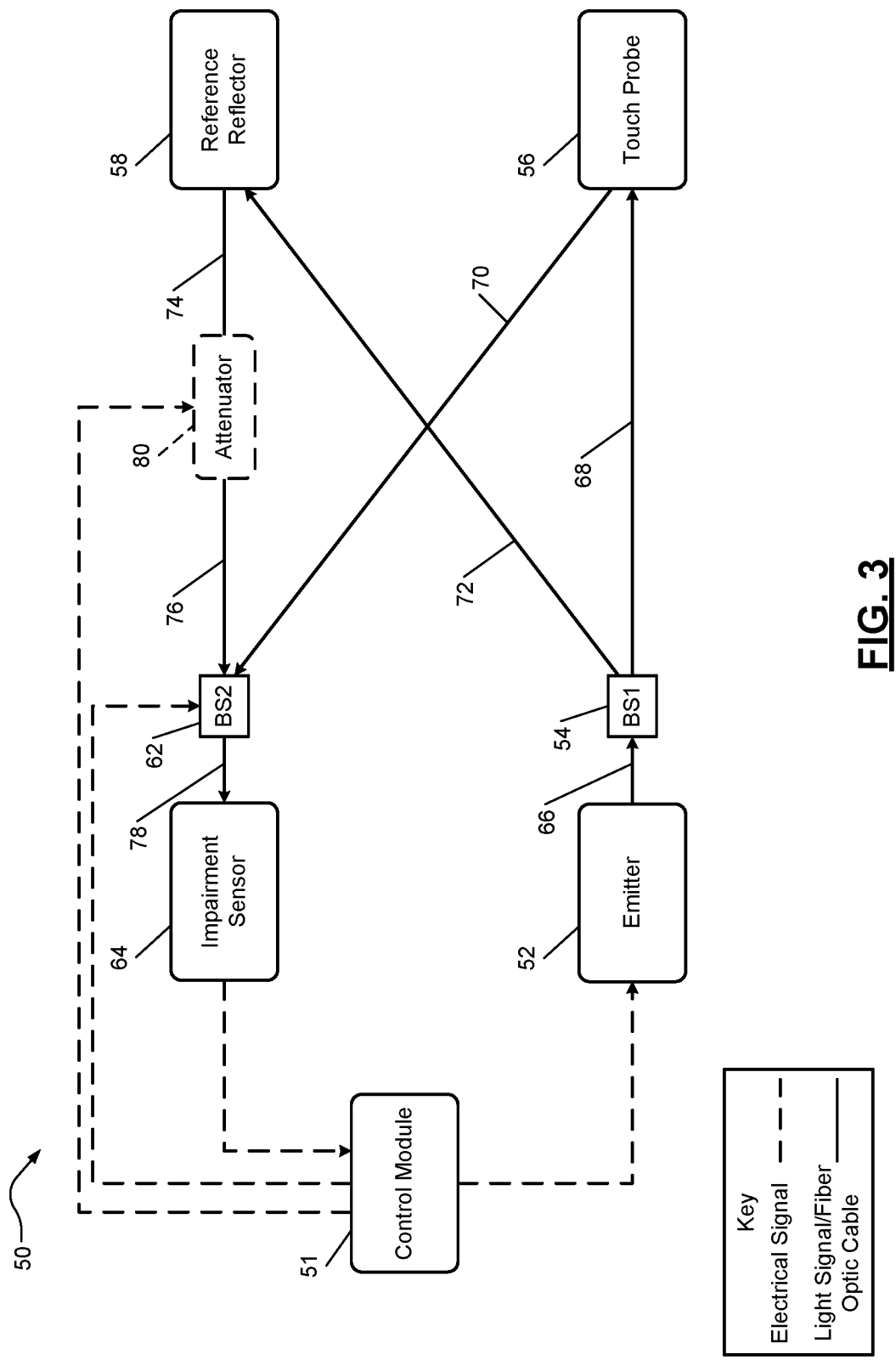
FIG. 3 is a functional block diagram of an example of a second impairment detection system including a reference reflector and not shutter in accordance with an embodiment of the present disclosure.

FIG. 3 shows a second impairment detection system 50 that includes a control module 51, an emitter 52, a first beam selector 54, a touch probe 56, a reference reflector 58, a second beam selector 62 and an impairment sensor 64 (e.g., a finger sensor or other suitable impairment sensor). The control module 51, emitter 52, beam selectors 54, 62, touch probe 56, and reference reflector 58 may operate and/or be configured similar as the control module 12, emitter 14, beam selectors 16, 24, touch probe 18, reference reflector 20 and impairment sensor 26 of FIG. 1.

The control module 51 signals the emitter 52 to generate a light signal, which is transmitted to the first beam selector 54 via a first fiber optic cable 66. The first light signal is sent from the first beam selector 54 to the touch probe 56 via a second fiber optic cable 68. The touch probe 56 emits the light signal and receives reflected light, which is transmitted via fiber optic cable 70 to the second beam selector 62. The first light signal is also transmitted from the first beam selector 54 to the reference reflector 58 via fiber optic cable 72. The light signal provided to the reference reflector 58 is reflected by the reference reflector 58 and transmitted to the second beam selector 62 via fiber optic cables 74, 76. The reference reflector 58 reflects the light from the fiber optic cable 72 to the fiber optic cable 74. The light signals received at the second beam selector 62 are provided to the impairment sensor 64 via fiber optic cable 78. In one embodiment, the second beam selector 62 is implemented as a DMD. Implementing the second beam selector 62 as a DMD instead of a beam splitter may minimize losses associated with the second beam selector 62.

Depending on the amount of attenuation associated with the reference reflector 58, an attenuator 80 may be included between the reference reflector 58 and the second beam selector 62. Since light is passed from the first beam selector 54 to the second beam selector 62, the light may be too intense for the impairment sensor 64. Thus, the attenuator 80 may be included. The attenuator 80 may reduce amplitudes of the reflected light signal to be within an appropriate input dynamic range of the impairment sensor 64. As an alternative the attenuator 80 may be connected between the first beam selector 54 and the reference reflector 58. The attenuator 80 may be controlled by the control module 102.

Figure 4:
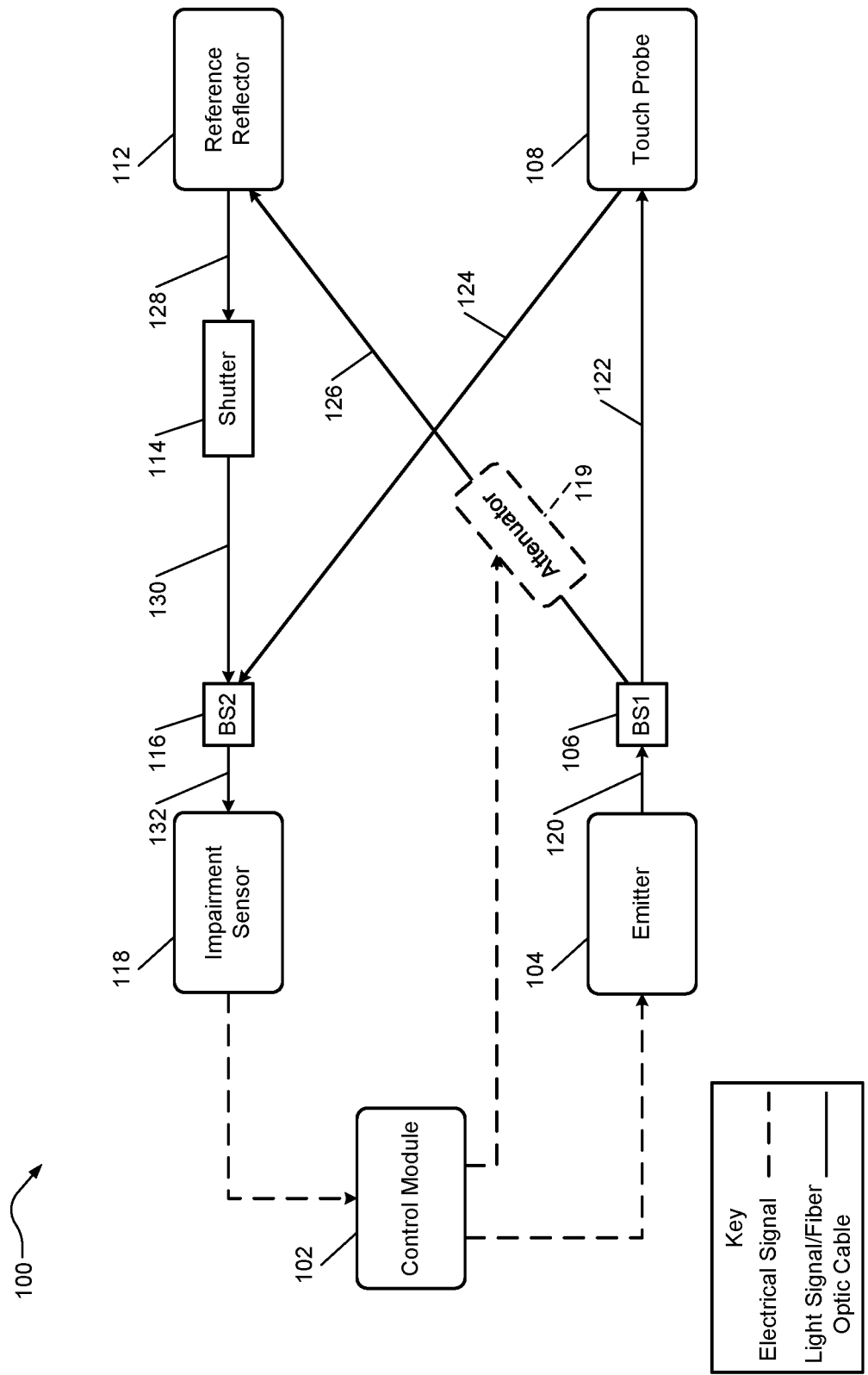
FIG. 4 is a functional block diagram of an example of a third impairment detection system including a reference reflector and a single shutter in accordance with an embodiment of the present disclosure.

FIG. 4 shows a third impairment detection system 100 that includes a control module 100, an emitter 104, a first beam selector 106, a touch probe 108, a reference reflector 112, a shutter 114, a second beam selector 116, and an impairment sensor 118 (e.g., a finger sensor or other suitable impairment sensor). The control module 102, emitter 104, beam selectors 106, 116, touch probe 108, and reference reflector 112 may operate and/or be configured similar as the control module 12, emitter 14, beam selectors 16, 24, touch probe 18, reference reflector 20 and impairment sensor 26 of FIG. 1.

The control module 102 signals the emitter 104 to generate a light signal, which is transmitted to the first beam selector 106 via a first fiber optic cable 120. The first light signal is sent from the first beam selector 106 to the touch probe 108 via a second fiber optic cable 122. The touch probe 108 emits the light signal and receives reflected light, which is transmitted via fiber optic cable 124 to the second beam selector 116. The first light signal is also sent from the first beam selector 106 to the reference reflector via fiber optic cable 126. The first light signal is reflected by the reference reflector 112 and transmitted to the second beam selector 116 and through the shutter 114 via fiber optic cables 128, 130. As an alternative, the shutter 114 may be connected between the first beam selector 106 and the reference reflector 112. As another alternative the shutter 114 may be located between (i) the first beam selector 106 and (ii) the touch probe 108 or the reference reflector 112. The reference reflector 112 reflects the light from the fiber optic cable 126 to the fiber optic cable 128. The light signals received at the second beam selector 116 are provided to the impairment sensor 118 via fiber optic cable 132.

Depending on the amount of attenuation associated with the reference reflector 112, an attenuator 119 may be included between the first beam selector 106 and the reference reflector 112. Since light is passed from the first beam selector 106 to the second beam selector 116 without passing through a shutter, the light may be too intense for the impairment sensor 118. Thus, the attenuator 119 may be included. The attenuator 119 may reduce amplitudes of the reflected light signal to be within an appropriate input dynamic range of the impairment sensor 118. As an alternative the attenuator 119 may be connected between the reference reflector 112 and the second beam selector 116. The attenuator 119 may be controlled by the control module 102.

Figure 5:
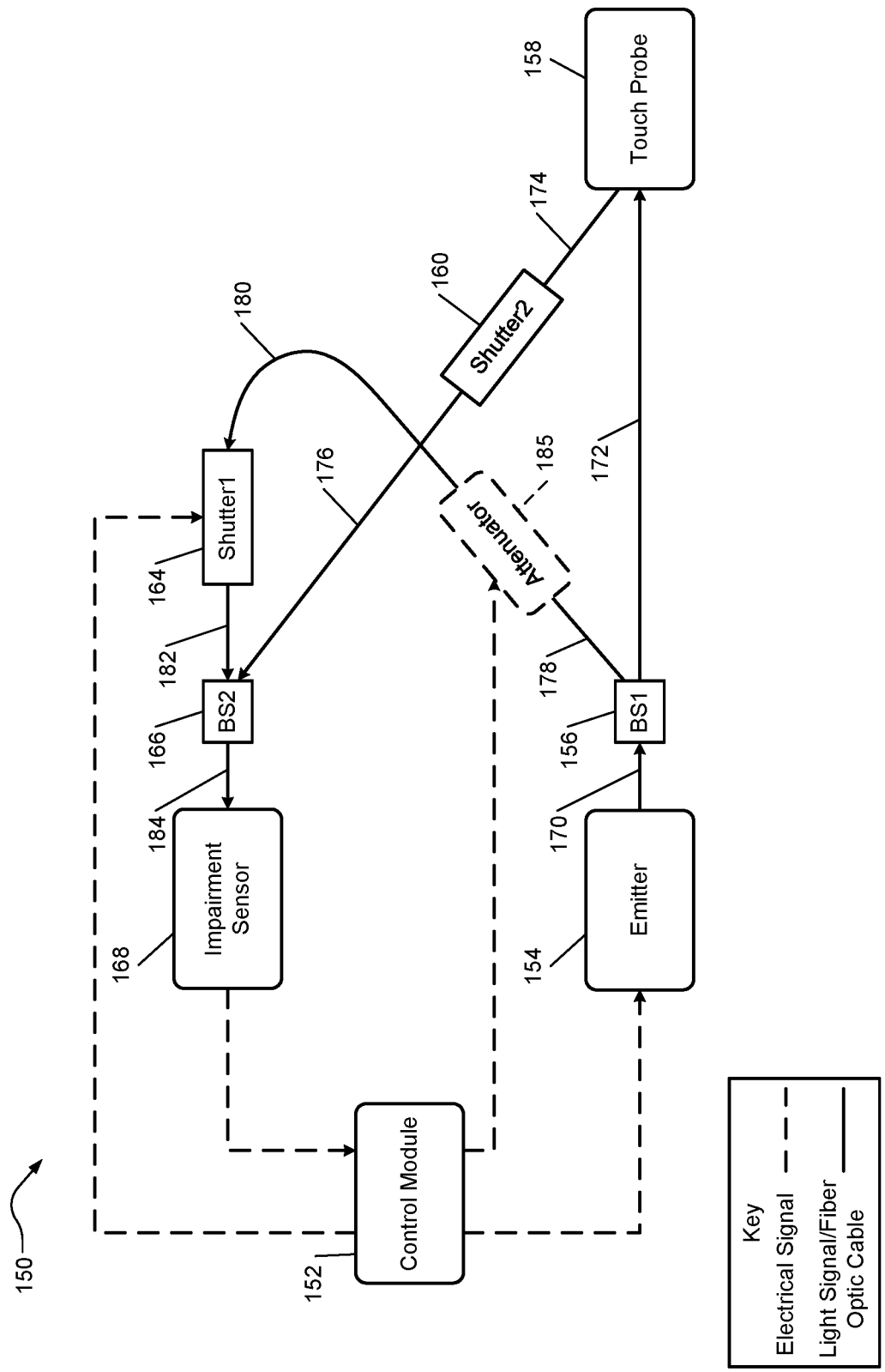
FIG. 5 is a functional block diagram of an example of a fourth impairment detection system including multiple shutters and no reference reflector in accordance with an embodiment of the present disclosure.

FIG. 5 shows a fourth impairment detection system 150 that includes a control module 152, an emitter 154, a first beam selector 156, a touch probe 158, shutters 160, 164, a second beam selector 166, and an impairment sensor 168 (e.g., a finger sensor or other suitable impairment sensor). The control module 152, emitter 154, beam selectors 156, 166, touch probe 158, shutters 160, 164, and impairment sensor 168 may operate and/or be configured similar as the control module 12, emitter 14, beam selectors 16, 24, touch probe 18, shutters 22, 23 and impairment sensor 26 of FIG. 1.

The control module 152 signals the emitter 154 to generate a light signal, which is transmitted to the first beam selector 156 via a first fiber optic cable 170. The first light signal is sent from the first beam selector 156 to the touch probe 158 via a second fiber optic cable 172. The touch probe 158 emits the light signal and receives reflected light, which is transmitted via fiber optic cables 174, 176 and the second shutter 160 to the second beam selector 166. The first light signal is also sent from the first beam selector 156 to the second beam selector 166 via fiber optic cables 178, 180, 182 and the first shutter 164. The light signals received at the second beam selector 166 are provided to the impairment sensor 168 via fiber optic cable 184.

Depending on the amount of attenuation associated with the first shutter 164, an attenuator 185 may be included between the first beam selector 156 and the first shutter 164. Since light is passed from the first beam selector 156 to the second beam selector 166 without being reflected by a reference reflector, the light may be too intense for the impairment sensor 168. Thus, the attenuator 185 may be included. The attenuator 185 may reduce amplitudes of the first light signal transmitted from the first beam selector 156 to the second shutter 164 to be within an appropriate input dynamic range of the impairment sensor 168. As an alternative the attenuator 185 may be connected between the first shutter 164 and the second beam selector 166. The attenuator 185 may be controlled by the control module 152.

Figure 6:
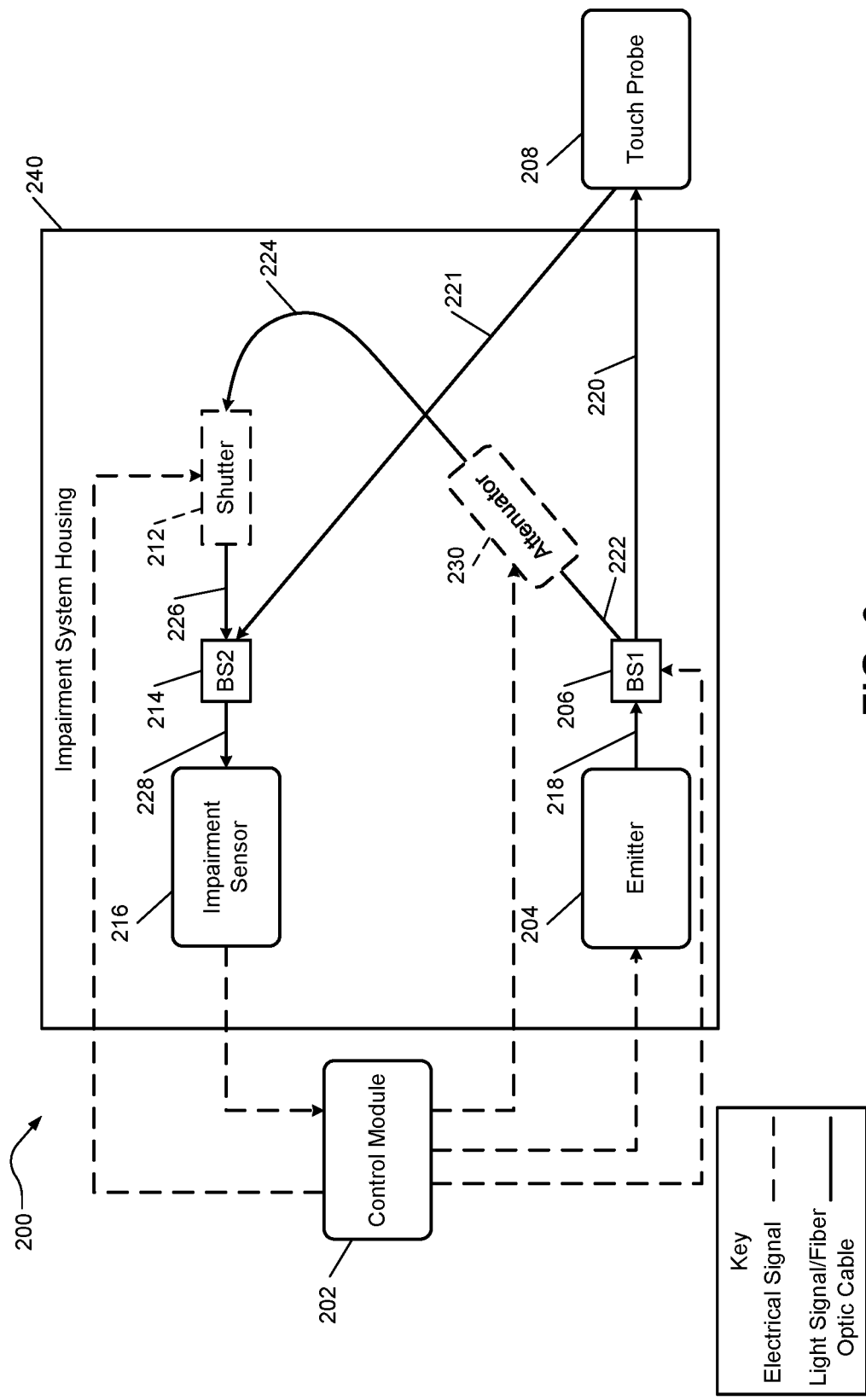
FIG. 6 is a functional block diagram of an example of a fifth impairment detection system including a single shutter and no reference reflector in accordance with an embodiment of the present disclosure.

FIG. 6 shows a fifth impairment detection system 200 that includes a control module 202, an emitter 204, a first beam selector 206, a touch probe 208, a shutter 212, a second beam selector 214 and a impairment sensor 216 (e.g., a finger sensor or other suitable impairment sensor). The shutter 212 is optional and may not be included. The control module 202, emitter 204, beam selectors 206, 214, touch probe 208, shutter 212 and impairment sensor 216 may operate and/or be configured similar as the control module 12, emitter 14, beam selectors 16, 24, touch probe 18, shutter 22 and impairment sensor 26 of FIG. 1.

The control module 202 signals the emitter 204 to generate a light signal, which is transmitted to the first beam selector 206 via a first fiber optic cable 218. The first light signal is sent from the first beam selector 206 to the touch probe 208 via a second fiber optic cable 220. In one embodiment, the first beam selector 206 is implemented as a DMD and controlled by the control module 202. The touch probe 208 emits the light signal and receives reflected light, which is transmitted via fiber optic cable 221 to the second beam selector 214. The first light signal is also sent from the first beam selector 206 to the second beam selector 166 via fiber optic cables 222, 224, 226 and the shutter 212. The light signals received at the second beam selector 214 are provided to the impairment sensor 216 via fiber optic cable 228.

An attenuator 230 may be included between the first beam selector 206 and the shutter 212. Since light is passed from the first beam selector 206 to the second beam selector 214 without being reflected by a reference reflector, the light may be too intense for the impairment sensor 216. Thus, the attenuator 230 may be included. The attenuator 230 may reduce amplitudes of the first light signal transmitted from the first beam selector 206 to the shutter 212 to be within an appropriate input dynamic range of the impairment sensor 216. As an alternative, the attenuator 230 may be connected between the shutter 212 and the second beam selector 206. The attenuator 230 may be controlled by the control module 202.

The emitter 204, beam selectors 206, 214, shutter 212, impairment sensor 216, and/or attenuator 230 may be included in an impairment system housing 240. Since the impairment detection system 200 includes a single sensor (i.e. the impairment sensor 216), the envelope and volume of the impairment system housing 240 is minimized. In one embodiment, the control module 202 and/or the touch probe 208 are also included in the impairment system housing 240.

Figure 7:
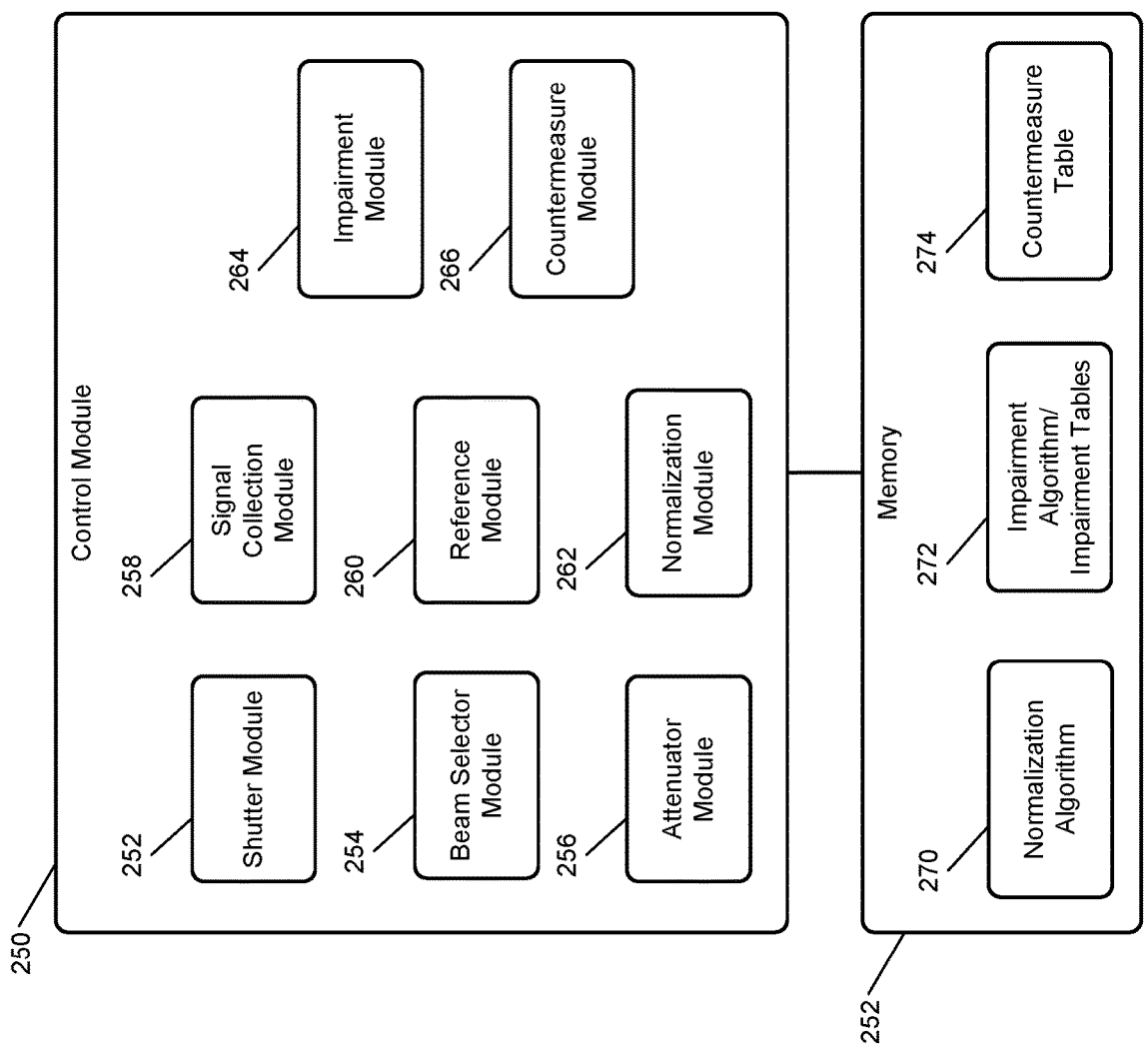
FIG. 7 is a functional block diagram of an example of a control module and a memory in accordance with an embodiment of the present disclosure.

FIG. 7 shows a control module 250 and a memory 252. The control module 250 may replace any of the control modules 12, 51, 102, 152, 202 of FIGS. 1-6. The control module 250 may include a shutter module 252, a beam selector module 254, an attenuator module 256, a signal collection module 258, a reference module 260, a normalization module 262, an impairment module 264 and/or a countermeasure module 266. The shutter module 252 controls operation of one or more shutters. The beam selector module 254 controls operation of one or more beam selectors (e.g., any of the beam selectors 16, 24, 54, 62, 106, 116, 156, 166, 206, 214 of FIGS. 1-6) and/or one or more corresponding DMDs. The attenuator module 256 controls operation of one or more attenuators (e.g., one of the attenuators 80, 119, 185, 230 of FIGS. 3-6) to control an amount of attenuation. The signal collection module 258 may receive an output from an impairment sensor (e.g., one of the impairment sensors 26, 64, 118, 168, 216 of FIGS. 1-6) and store the output in the memory 252.

The reference module 260 determines reference parameters based on which to normalize a light signal received from a touch probe (e.g., one of the touch probes 18, 56, 108, 158, 208). The reference parameters may indicate amplitudes, power levels, frequencies, duty cycles, etc. of light signals transmitted from a first beam selector (e.g., one of the first beam selectors 16, 54, 106, 156, 206 of FIGS. 1-6) to a reference reflector (one of the reference reflectors 20, 58, 112 of FIGS. 1-3) and/or a second beam selector (one of the second beam selectors 24, 62, 116, 166, 214 of FIGS. 1-6). The normalization module 262 normalizes the light signal received from the touch probe (one of the touch probes 18, 56, 108, 158, 208 of FIGS. 1-6). The normalization may be based on a normalization algorithm 270 stored in the memory 252.

The impairment module 264 determines an impairment type and/or level based on results of the normalization performed by the normalization module 262. The impairment type may refer to the chemical and/or corresponding impairment state of an individual. For example, if the chemical being detected is alcohol, the impairment type may indicate that legal intoxication due to alcohol is being determined. The results may include normalized power levels, amplitudes, and/or other normalized parameters. The impairment type and/or level may be determined based on an impairment algorithm, one or more transfer functions, and/or impairment tables 272 stored in the memory 252. The impairment tables may relate normalization values to impairment types and/or levels.

The countermeasure module 266 performs a countermeasure based on the impairment level. The countermeasure may be determined based on a countermeasure table 274 that relates impairment levels to countermeasures. Some example countermeasures include: generating of an alert signal; limiting and/or preventing access to certain areas of a company; limiting and/or preventing access to one or more buildings; limiting and/or preventing computer access; reducing and/or changing an employee access and/or authorization level; preventing entrance into a vehicle; preventing operation of a vehicle, a vehicle engine and/or a vehicle motor; etc. Operations of the impairment detection systems of FIGS. 1-6 and modules 250, 252, 254, 256, 258, 260, 262, 264, 266 are further described below with respect to the method of FIGS. 9-10.

Figure 8:
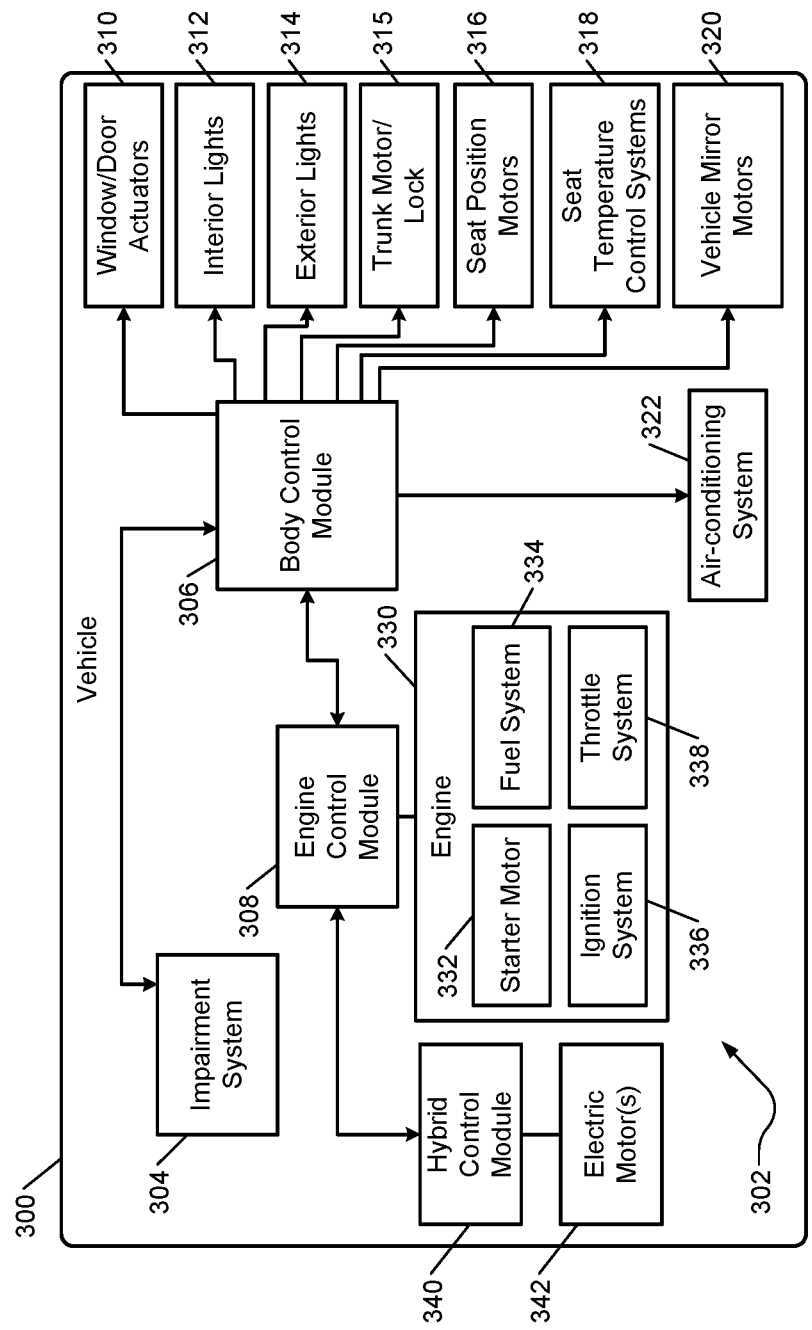
FIG. 8 is a functional block diagram of an example of a vehicle including a vehicle system and an impairment detection system in accordance with an embodiment of the present disclosure.

FIG. 8 shows a vehicle 300 including a vehicle system 302 and an impairment detection system 304. The vehicle 300 includes a body control module 306 and an engine control module 308. The body control module 306 controls operations of certain vehicle components, motors, and systems, such as window and door actuators 310, interior lights 312, exterior lights 314, a trunk motor and lock 315, seat position motors 316, seat temperature control systems 318 vehicle mirror motors 320 (e.g., side view motors and rear view motor), and air-conditioning system 322. The body control module 306 may control the components, motors, and systems based on a detected impairment level determined by the impairment system 304. As an example, the body control module 306 may limit and/or prevent operation of certain components, motors, and/or systems until an impairment test is performed of a person entering the vehicle 300. As another example, the body control module 306 may limit and/or prevent operation of certain components, motors and/or systems based on an impairment level determined by performing the impairment test.

The engine control module 308 controls operation of an engine 330 of the vehicle 14. The engine 330 may include a starter motor 332, a fuel system 334, an ignition system 336 and a throttle system 338. The engine control module 308 may control operation of the starter motor 332, the fuel system 334, the ignition system 336 and the throttle system 338 based on signals from the impairment system 304. The impairment system 304 may, for example, signal the engine control module 308 to start and/or stop the engine 330 based on whether an impairment test has been performed and/or based on an impairment level of a vehicle operator, which may be received from the body control module 306. The starting and stopping of the engine 330 may include: running the starter motor 332; enabling the fuel system 334 to start supplying fuel to the engine 330; disabling the fuel system 334 to stop supplying fuel to the engine 330; enabling the ignition system 336 to provide spark to cylinders of the engine 330; disabling spark to the cylinders of the engine 330; and adjusting position of a throttle of the throttle system 338.

The vehicle 300 may include a hybrid control module 340 that controls operation of one or more electric motors 342. The hybrid control module 340 may control operation of the motors 342 based on whether an impairment test has been performed and/or based on an impairment level of a vehicle operator received from the body control module 306. This may include running and/or stopping the motors 342.

While FIG. 8 shows a vehicle example for implementation of the impairment detection systems of FIGS. 1-6 and the control module and memory of FIG. 7, the embodiments disclosed herein are applicable to non-vehicle implementations. For further defined structure of the modules of FIGS. 1-8 see below provided methods of FIGS. 9-12 and below provided definition for the term "module". The systems disclosed herein may be operated using numerous methods, an example method is illustrated in FIG. 9.

Figure 9:
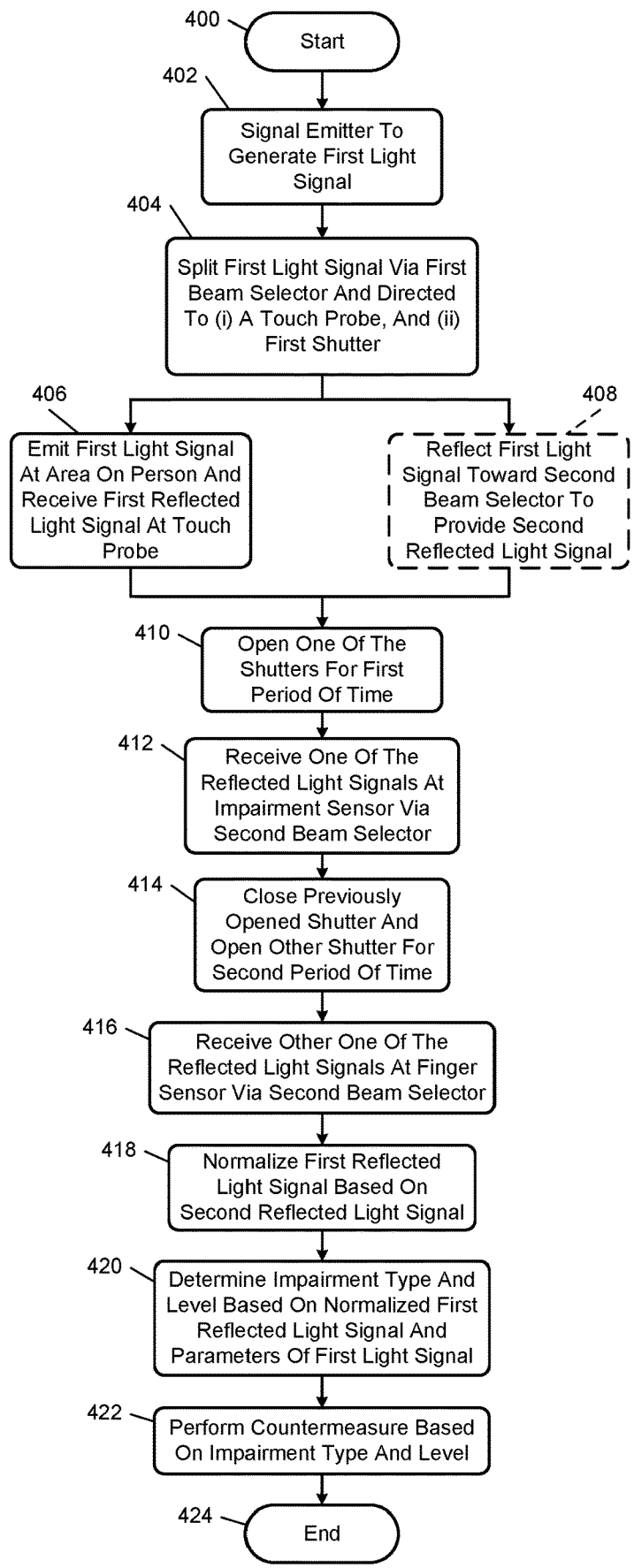
FIG. 9 illustrates an example of an impairment and countermeasure method corresponding to the examples of FIGS. 1-2 and 5 and for determining and responding to an impairment level of a person in accordance with an embodiment of the present disclosure.

FIG. 9 illustrates an impairment and countermeasure method corresponding to the systems of FIGS. 1 and 5 and for determining and responding to an impairment level of a person. Although the following operations are primarily described with respect to the implementations of FIGS. 1, 5 and 7, the operations may be modified to apply to other implementations of the present disclosure. The operations may be iteratively performed. The method may begin at 400. At 402, the emitter 14 (or 154) generates a first light signal. At 404, the first light signal is split via the first beam selector 16 (or 156) and directed to (i) the touch probe 18 (or 158), and (ii) a first shutter 22 (or shutter 164).

At 406, the touch probe 18 (or 158) emits the first light signal at an area on a person (e.g., a tip of a finger of the person) and receives a first reflected light signal. At 408, the first light signal may be received from the first beam selector 16 (or 156) and (i) reflected by the reference reflector 20 to the first shutter 22, or (ii) directly transmitted to the first shutter 164. Operation 406 may be performed while operation 408 is performed.

At 410, one of the shutters 22, 23 (or 160, 164) is opened while the other one of the shutters 22, 23 (or 160, 164) is closed. At 412, one of the first reflected light signal and the second reflected light signal are received at the impairment sensor 26 (or 168) via the second beam selector 24 (or 166).

At 414, the previously opened shutter is closed and the other one of the shutters 22, 23 (or 160, 164) is opened. At 416, the other one of the first reflected light signal and the second reflected light signal is received at the impairment sensor 26 (or 168) via the second beam selector 24 (or 166).

At 418, the normalization module 262 normalizes the first reflected light signal based on the second reflected light signal. The second reflected light signal is used as a reference signal. At 420, the impairment module 264 determines an impairment type and/or impairment level based on the normalized first reflected light signal and parameters of the first reflected light signal. The impairment module 264 may indicate whether the person is legally intoxicated based on the impairment level.

At 422, the countermeasure module 266 may perform a countermeasure based on the impairment level. For example, if the impairment level is greater than a predetermined threshold, one or more countermeasures may be performed. This may include any of the above-stated countermeasures including generating an alert signal, preventing access to files on a computer, to a computer system, to an area of a building, to an interior of a vehicle, etc. This may include refraining from unlocking one or more doors. The countermeasures may include preventing activation/ignition of a vehicle and/or other countermeasures. The method may end at 424.

Figure 10:
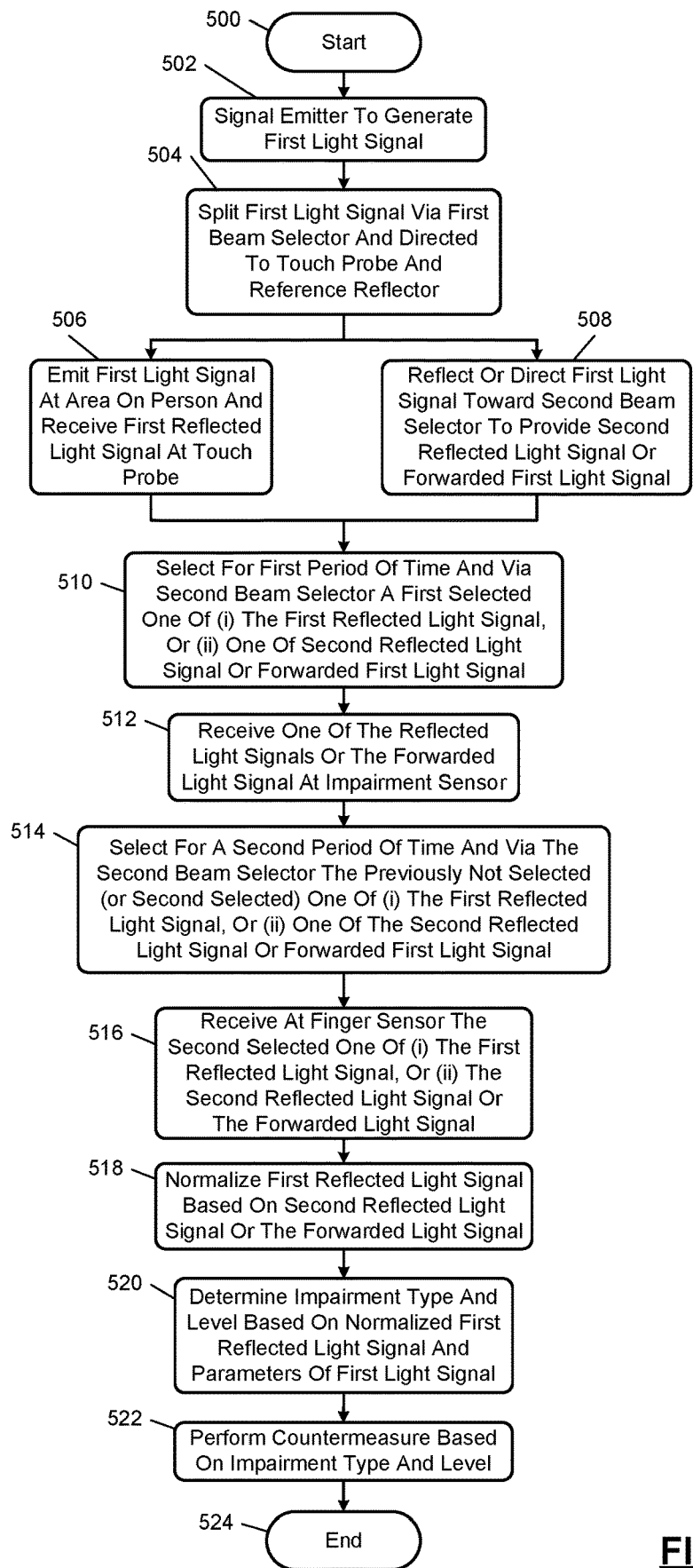
FIG. 10 illustrates an example of an impairment and countermeasure method corresponding to the examples of FIGS. 3 and 6 and for determining and responding to an impairment level of a person in accordance with an embodiment of the present disclosure.

FIG. 10 shows an impairment and countermeasure method corresponding to the examples of FIGS. 3 and 6. The method of FIG. 10 is described as if the shutter 212 of FIG. 6 is not included and the first light signal out of the first beam selector 206 is provided to the second beam selector 214 without passing through the shutter 212. The second beam selector 62 (or 214) may be a DMD or other beam selector. Although the following operations are primarily described with respect to the implementations of FIGS. 3 and 6-7, the operations may be modified to apply to other implementations of the present disclosure. The operations may be iteratively performed. The method may begin at 500. At 502, the emitter 52 (or 204) generates a first light signal. At 504, the first light signal is split via the first beam selector 54 (or 206) and directed to (i) the touch probe 56 (or 208), and (ii) the second beam selector 62 (or 214). The first light signal may be transmitted to the second beam selector 62 via the reference reflector 58.

At 506, the touch probe 56 (or 208) emits the first light signal at an area on a person and receives a first reflected light signal. At 508, the first light signal may be (i) reflected by the reference reflector 58 to the second beam selector 62 to provide a second reflected light signal, or (ii) directly transmitted to the second beam selector 62. When directly transmitted, the first light signal is referred to the forwarded light signal. Operation 506 may be performed while operation 508 is performed.

At 510, the second beam selector 62 (or 214) selects for a first period of time a first selected one of (i) the first reflected light signal, or (ii) one of the second reflected light signal or the forwarded first light signal. At 512, the impairment sensor 64 (or 216) receives the output of the second beam selector 62. At 514, the second beam selector 62 (or 214) selects for a second period of time a previously not selected (or second selected) one of (i) the first reflected light signal, or (ii) one of the second reflected light signal or the forwarded first light signal. At 516, the impairment sensor 64 (or 216) receives the second selected one of (i) the first reflected light signal, or (ii) one of the second reflected light signal or the forwarded first light signal.

At 518, the normalization module 262 normalizes the first reflected light signal based on the second reflected light signal or the forwarded light signal. The second reflected light signal or the forwarded light signal is used as a reference signal. At 520, the impairment module 264 determines an impairment type and/or impairment level based on the normalized first reflected light signal and parameters of the first reflected light signal. At 522, the countermeasure module 266 may perform a countermeasure based on the impairment level. For example, if the impairment level is greater than a predetermined threshold, one or more countermeasures may be performed. This may include any of the above-stated countermeasures. The method may end at 524.

Figure 11:
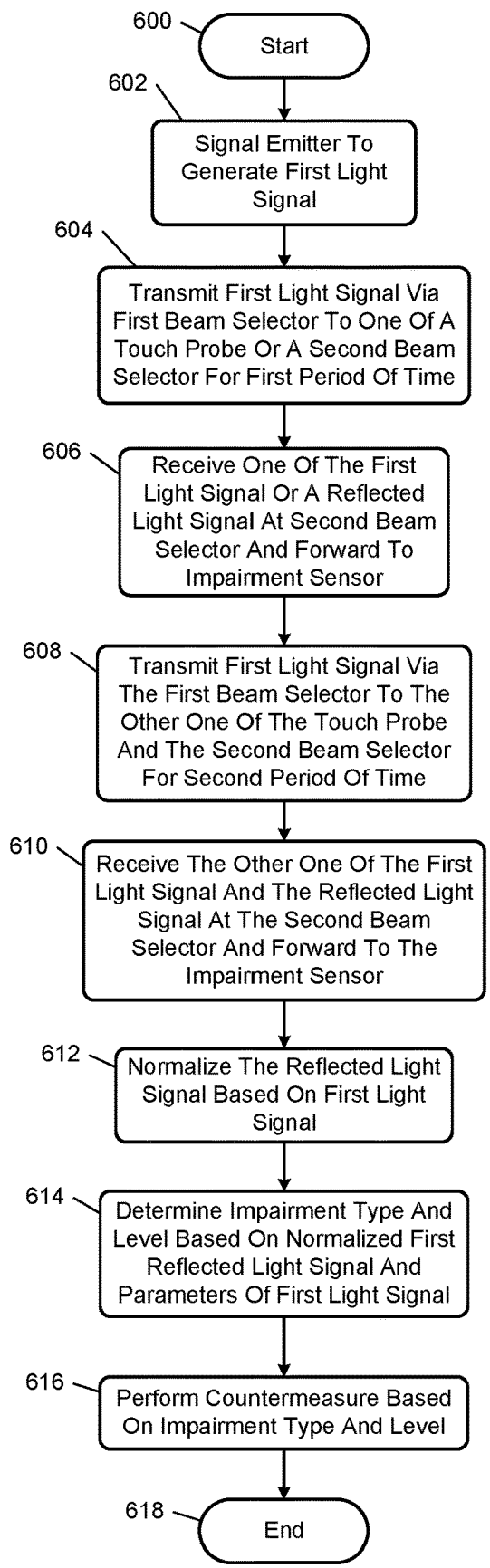
FIG. 11 illustrates another example of an impairment and countermeasure method corresponding to the examples of FIGS. 3 and 6 and for determining and responding to an impairment level of a person in accordance with an embodiment of the present disclosure.

FIG. 11 shows an impairment and countermeasure method corresponding to the examples of FIGS. 3 and 6. The method of FIG. 11 is described as if the shutter 212 of FIG. 6 is not included and the first light signal out of the first beam selector 206 is provided to the second beam selector 214 without passing through the shutter 212. The first beam selector 54 (or 206) may be a DMD or other beam selector. Although the following operations are primarily described with respect to the implementations of FIGS. 3 and 6-7, the operations may be modified to apply to other implementations of the present disclosure. The operations may be iteratively performed. The method may begin at 600. At 602, the emitter 52 (or 204) generates a first light signal.

At 604, the first light signal is transmitted via the first beam selector 54 (or 206) to the touch probe 56 (or 208) or to the second beam selector 62 (or 214) for a first period of time. At 606, the second beam selector 62 (or 214) receives one of a reflected light signal from the touch probe 56 (or 208) or the first light signal from the first beam selector 54 (or 206) and forwards the received signal to the impairment sensor 64 (or 216).

At 608, the first light signal is transmitted via the first beam selector to the other one of the touch probe 56 (or 208) or the second beam selector 62 (or 214) for a second period of time. At 610, the second beam selector 62 (or 214) receives the other one of the reflected light signal or the first light signal and forwards the received signal to the impairment sensor 64 (or 216).

At 612, the normalization module 262 normalizes the reflected light signal based on the first light signal. The first light signal is used as a reference signal. At 614, the impairment module 264 determines an impairment type and/or impairment level based on the normalized first reflected light signal and parameters of the first reflected light signal. At 616, the countermeasure module 266 may perform a countermeasure based on the impairment level. For example, if the impairment level is greater than a predetermined threshold, one or more countermeasures may be performed. This may include any of the above-stated countermeasures. The method may end at 618.

Figure 12:
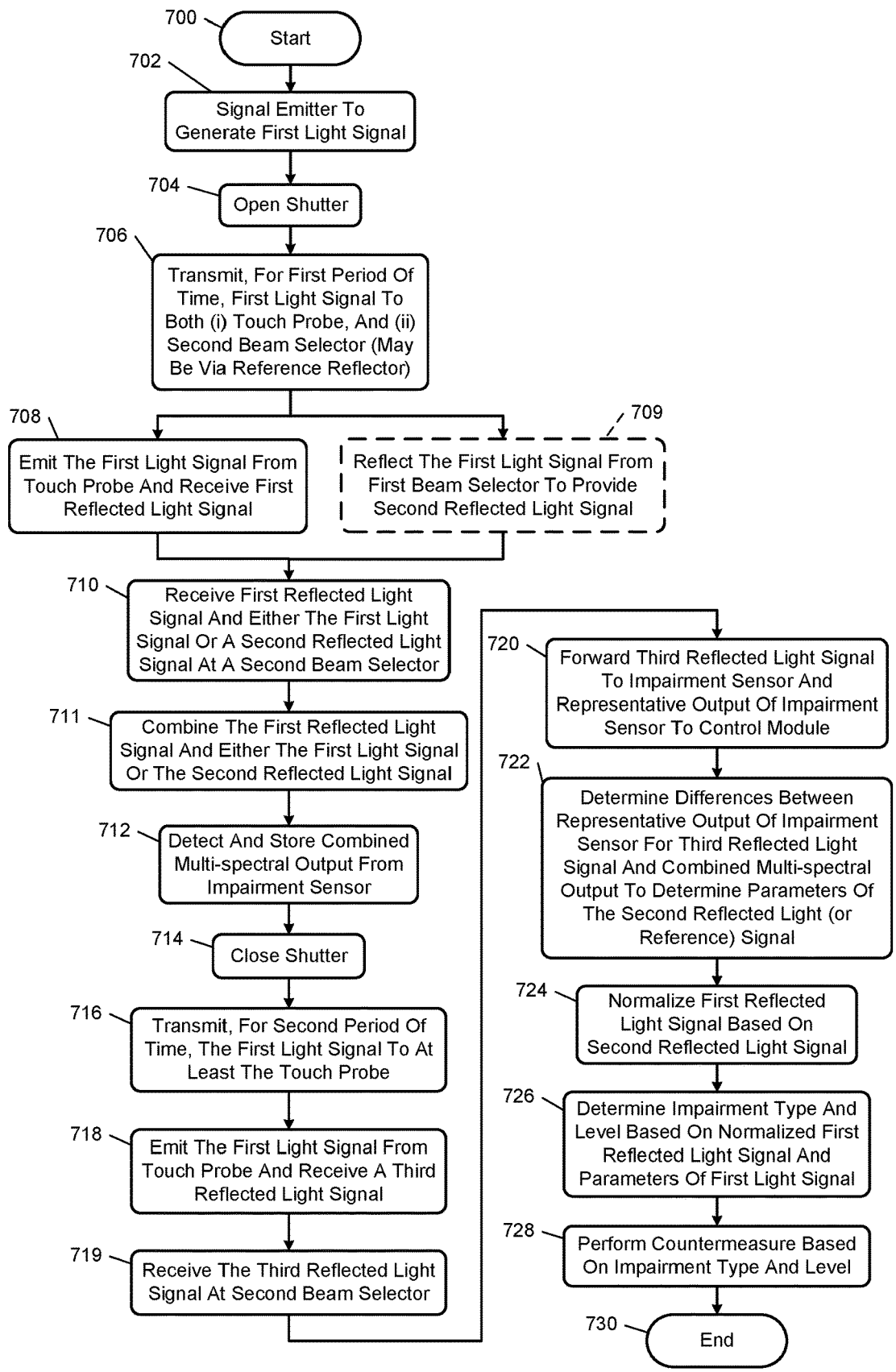
FIG. 12 illustrates another example of an impairment and countermeasure method corresponding to the examples of FIGS. 4 and 6 and for determining and responding to an impairment level of a person in accordance with an embodiment of the present disclosure.

FIG. 12 shows an impairment and countermeasure method corresponding to the examples of FIGS. 4 and 6. The method of FIG. 12 is described as if the shutter 114 (or 212) of FIGS. 4 and 6 is included. Although the method of FIG. 12 is described as including the shutter 114 (or 212) as being located between the reference reflector 112 and the second beam selector 116 or between the first beam selector 206 and the second beam selector 214, the method of FIG. 12 may be modified for when the shutter 114 (or 212) is located between the first beam selector 106 (206) and the touch probe 108 (or 208) or between the touch probe 108 (or 208) and the second beam selector 116 (or 214). The first beam selector 106 (or 206) and the second beam selector 116 (or 214) may be configured respectively as a beam splitter and a beam combiner. Although the following operations are primarily described with respect to the implementations of FIGS. 4 and 6-7, the operations may be modified to apply to other implementations of the present disclosure. The operations may be iteratively performed. The method may begin at 700. At 702, the emitter 104 (or 204) generates a first light signal. At 704 the shutter 114 (or 212) is opened.

At 706, the first light signal is transmitted for a first period of time to both (i) the touch probe 108 (or 208), and (ii) the second beam selector 116 (or 214). At 708, the touch probe emits the first light signal and receives a first reflected light signal. At 709, the first light signal may be reflected off of the reference reflector 112 and passed through the shutter 114 prior to being received at the second beam selector 116 to provide a second reflected light signal.

At 710, the first reflected light signal and either the first light signal or the second reflected light signal are received at the second beam selector 116 (or 214). At 711, the second beam selector 116 (or 214) combines (i) the first reflected light signal and (ii) either the first light signal or the second reflected light signal.

At 712, the control module 102 (or 202) detects and stores a combined multi-spectral output from the impairment sensor 118 (or 216). The combined multi-spectral output is based on the combination of (i) the first reflected light signal and (ii) either the first light signal or the second reflected light signal.

At 714, the shutter 114 (or 212) is closed. At 716, the first light signal is transmitted from the emitter 104 (or 204) to at least the touch probe 108 (or 208). At 718, the first light signal is emitted from the touch probe 108 (or 208) and a reflected light signal (or third reflected light signal) is received at the touch probe 108 (or 208). The third reflected light signal may match (i.e. have same power, frequencies, duty cycles, etc.) as the first reflected light signal. At 719, the second beam selector 116 (or 214) receives the third reflected light signal received at 716.

At 720, the third reflected light signal is forwarded to the impairment sensor 118 (or 216) and an output of the impairment sensor 118 (or 216) representative of the third reflected light signal is provided to the control module 102 (or 202). At 722, the control module 102 (or 202) determines differences between (i) the output of the impairment sensor 118 (or 216) that is representative of the third reflected light signal, and (ii) the combined multi-spectral output, to determine the second reflected light signal and/or parameters of the second reflected light signal. The parameters of the second reflected light signal are used as reference parameters.

At 724, the normalization module 262 normalizes the first reflected light signal based on the second reflected light signal and/or corresponding properties of the second reflected light signal. The second reflected light signal or the forwarded light signal is used as a reference signal. The above-described operations 706, 708, 709, 710, 711, 712, 716, 718, 719, 720, 722, 724 may be changed accordingly if the shutter 114 (or 164) is located in a different location. At 726, the impairment module 264 determines an impairment type and/or impairment level based on the normalized first reflected light signal and parameters of the first reflected light signal. At 728, the countermeasure module 266 may perform a countermeasure based on the impairment level. For example, if the impairment level is greater than a predetermined threshold, one or more countermeasures may be performed. This may include any of the above-stated countermeasures. The method may end at 730.

The above-described operations of FIGS. 9-12 are meant to be illustrative examples; the operations may be performed sequentially, synchronously, simultaneously, continuously, during overlapping time periods or in a different order depending upon the application. Also, any of the operations may not be performed or skipped depending on the implementation and/or sequence of events.

The above-described systems and methods account for drift in touch probe outputs and drift in sensor sensitivity by including reference channels having outputs indicative of parameters of light signals provided to the touch probes. This allows the outputs of the touch probes to be normalized and correlated to provide impairment levels. The reference channels also provide feedback to correct measured values for system diagnostics and system response adjustment. For example, the control module disclosed herein may adjust parameters of emitted signals based on detected outputs of the disclosed impairment sensors to account for drift and to assure that the parameters utilized are appropriate for the type of chemical and/or drug scanning being performed. The systems utilize a single light source and multi-spectral sensor to provide both reference samples and user samples without operator action to change a configuration of the systems. The use of a single light source and sensor minimize system complexity, size and costs. Also, components of the system may be located on a single side of a housing away from a touch probe. The systems and method provide enhanced reliability of impairment detection including compensating for laser, fiber optic and environmental variation over time.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for," or in the case of a method claim using the phrases "operation for" or "step for."

What is claimed is:

1. An impairment detection system comprising:
   an emitter configured to emit a first light signal;
   a first beam selector configured to forward at least a first portion of the first light signal to a touch probe;
   a reference reflector configured to reflect at least a second portion of the first light signal received from the first beam selector to generate a second reflected signal;
   a second beam selector configured to receive (i) a first reflected signal from the touch probe based on reflection of the at least the first portion of the first light signal on an area of a person, and (ii) the second reflected signal,
   a device configured to control forwarding of the at least the first portion of the first light signal, the at least the second portion of the first light signal, the first reflected signal, or the second reflected signal, such that the second beam selector (i) receives the first reflected signal and the second reflected signal during a first period of time, and (ii) receives only one of the first reflected signal and the second reflected signal during a second period of time;
   a sensor configured to receive from the second beam selector the first reflected signal and the second reflected signal; and
   a control module configured to determine an impairment level of the person based on an output of the sensor.

2. The impairment detection system of claim 1, further comprising:
   a first shutter; and
   a second shutter,
   wherein the control module is configured to
      open the first shutter to permit passage of the second reflected signal to the second beam selector, and
      open the second shutter to permit passage of the first reflected signal to the second beam selector.

3. The impairment detection system of claim 1, further comprising the touch probe, wherein the touch probe is configured to receive the at least the first portion of the first light signal, emit the at least the first portion of the first light signal at an area on the person, and receive the first reflected signal.

4. The impairment detection system of claim 1, wherein the second beam selector:
   during the first period of time, selects one of the first reflected signal and the second reflected signal, and
   during the second period of time, selects the other one of the first reflected signal and the second reflected signal.

5. The impairment detection system of claim 1, wherein the device is implemented as a shutter and is configured to permit passage of the first reflected signal or the second reflected signal to the second beam selector, wherein the control module is configured to:
   receive a combined spectral output signal from the second beam selector during the first period of time;
   receive an output representative of one of the first reflected signal or the second reflected signal from the second beam selector during the second period of time;
   compare the combined spectral output signal to the output representative of one of the first reflected signal or the second reflected signal; and
   based on the comparison, determine the impairment level of the person.

6. The impairment detection system of claim 1, further comprising:
   a first shutter configured to permit passage of the first reflected signal from the touch probe to the second beam selector; and
   a second shutter configured to permit passage of the at least the second portion of the first light signal from the first beam selector to the second beam selector.

7. The impairment detection system of claim 1, further comprising an attenuator configured to attenuate the second reflected signal prior to being received at the second beam selector.

8. The impairment detection system of claim 1, wherein the first beam selector is configured to:
   transmit the first light signal to the touch probe and not the second beam selector during the second period of time; and
   transmit the first light signal to the second beam selector and not the touch probe during a third period of time.

9. The impairment detection system of claim 8, further comprising an attenuator configured to attenuate the at least the second portion of the first light signal and provide the attenuated first light signal to the second beam selector.

10. An impairment detection system comprising:
    an emitter configured to emit a first light signal;
    a first beam selector configured to forward at least a first portion of the first light signal to a touch probe;
    a second beam selector configured to receive at least a second portion of the first light signal and a reflected light signal from the touch probe based on reflection of the at least the first portion of the first light signal on an area of a person, wherein the at least the second portion of the first light signal is provided from at least one of the emitter or the first beam selector to the second beam selector without being reflected off a reflector;
    a sensor configured to receive from the second beam selector the at least the second portion of the first light signal and the reflected light signal; and
    a control module configured to determine an impairment level of the person based on an output of the sensor.

11. The impairment detection system of claim 10, further comprising:
   a first shutter; and
   a second shutter,
   wherein the control module is configured to
      open the first shutter to permit passage of the at least the second portion of the first light signal to the second beam selector, and
      open the second shutter to permit passage of the reflected light signal to the second beam selector.

12. The impairment detection system of claim 10, further comprising the touch probe, wherein the touch probe is configured to receive the at least the first portion of the first light signal, emit the at least the first portion of the first light signal at an area on the person, and receive the reflected light signal.

13. The impairment detection system of claim 10, wherein the second beam selector:
   during a first period of time, selects one of the at least the second portion of the first light signal and the reflected light signal, and
   during a second period of time, selects the other one of the at least the second portion of the first light signal and the reflected light signal.

14. The impairment detection system of claim 10, further comprising a shutter configured to permit passage of the at least the second portion of the first light signal or the reflected light signal from the first beam selector to the second beam selector, wherein:
   the second beam selector is configured to (i) receive the at least the second portion of the first light signal and the reflected light signal during a first period of time, and (ii) receive one of the at least the second portion of the first light signal and the reflected light signal during a second period of time; and
   the control module is configured to
      receive a combined spectral output signal from the second beam selector during the first period of time,
      receive an output representative of one of the first light signal and the reflected light signal from the second beam selector during the second period of time,
      compare the combined spectral output signal to the output representative of the one of the first light signal and the reflected light signal, and
      based on the comparison, determine the impairment level of the person.

15. The impairment detection system of claim 10, further comprising:
   a first shutter configured to permit passage of the at least the second portion of the first light signal from the first beam selector to the second beam selector; and
   a second shutter configured to permit passage of the reflected light signal from the touch probe to the second beam selector.

16. The impairment detection system of claim 10, further comprising a shutter configured to prevent passage of one of the at least the second portion of the first light signal and the reflected light signal to the second beam selector during a first period of time and not during a second period of time,
   wherein the second beam selector receives both the at least the second portion of the first light signal and the reflected light signal during the second period of time.

17. The impairment detection system of claim 10, further comprising an attenuator configured to attenuate the at least the second portion of the first light signal prior to being received at the second beam selector.

18. The impairment detection system of claim 10, further comprising an attenuator configured to attenuate the at least the second portion of the first light signal and provide the attenuated at least the second portion of the first light signal to the second beam selector, wherein the first beam selector is configured to:
   transmit the first light signal to the touch probe and not the second beam selector during a first period of time; and
   transmit the first light signal to the second beam selector and not the touch probe during a second period of time.

19. The impairment detection system of claim 1, wherein the first beam selector comprises the device or the device is implemented as a shutter.

* * * * *